(12) United States Patent
Matthiessen et al.

(10) Patent No.: US 6,777,390 B1
(45) Date of Patent: Aug. 17, 2004

(54) STABLE BLOOD COAGULATION INHIBITOR-FREE FACTOR VII PREPARATION AND METHOD FOR PREPARING SAME

(75) Inventors: Peter Matthiessen, Vienna (AT); Peter Turecek, Klosterneuburg (AT); Hans-Peter Schwarz, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/719,945
(22) PCT Filed: Jun. 14, 1999
(86) PCT No.: PCT/AT99/00154

§ 371 (c)(1),
(2), (4) Date: Feb. 20, 2001

(87) PCT Pub. No.: WO99/66031

PCT Pub. Date: Dec. 23, 1999

(30) Foreign Application Priority Data

Jun. 17, 1998 (AT) .......................................... A 1043/98

(51) Int. Cl.[7] .............................................. A61K 38/00
(52) U.S. Cl. ........................................................ 514/21
(58) Field of Search ........................... 514/21; 530/350, 530/412, 2, 384; 424/529, 530, 94.64; 435/69.6, 68.1

(56) References Cited

U.S. PATENT DOCUMENTS

| | | | | |
|---|---|---|---|---|
| 4,357,321 A | * | 11/1982 | Thomas | 424/529 |
| 4,456,591 A | * | 6/1984 | Thomas | 424/94.64 |
| 5,344,918 A | | 9/1994 | Dazey et al. | |
| 5,593,968 A | * | 1/1997 | Turecek et al. | 435/68.1 |
| 5,700,914 A | * | 12/1997 | Jørgensen et al. | 530/384 |
| 6,013,620 A | * | 1/2000 | Turecek et al. | 424/530 |
| 6,039,944 A | * | 3/2000 | Berkner et al. | 424/94.64 |

FOREIGN PATENT DOCUMENTS

| | | |
|---|---|---|
| EP | 83850180.7 A | 1/1985 |
| EP | 89118199.2 B | 2/1994 |
| JP | 8-237146 A | 3/1998 |
| WO | 94/22905 A | 10/1994 |

OTHER PUBLICATIONS

GJ Broze, Jr and PW Majerus. Purification and properties of human coagulation factor VII. J. Biol. Chem. 1980 255: 1242–1247.*

JH Lawson and KG Mann. Cooperative activation of human factor IX by the human extrinsic pathway of blood coagulation. J. Biol. Chem. 1991 266: 11317–11327.*

Scopes RK. Protein Purification. Springer–Verlag New York, 1987, pp. 119–126.*

Adam N. Goldfarb, Kristine Lewandowska, and Cristopher A. Pennell. Identification of a Highly Conserved Module in E Proteins Required for in Vivo Helix–loop–helix Dimerization. J. Biol. Chem. 1998 273: 2866–2873.*

Sigma Chemical Company, 1997. Factor VII, Product No. F6509, p. 427.*

*Chemical Abstracts* vol. 100, 1984.

63–*Pharmaceuticals* vol. 102, 1985.

S. Paul Bajaj, Samuel I. Rapaport, Stephen F. Brown; *Isolation and Characterization of Human Factor VII;* The Journal of Biological Chemistry; vol. 254, No. 1, pp. 253–259; Publication date: Dec. 20, 1980 and Revised on: Jul. 21, 1980.

U. Hedner, S. Bjoern, S.S. Bernvil, L. Tengborn, L. Stigendahl; *Clinical Experience with Human Plasma–Derived Factor VIIa in Patients with Hemophilia A and High Titer Inhibitors;* Haemostasis 1989; 19:335–343.

Peter Wildgoose and Walter Kisiel; *Activation of Human Factor VII by Factors IXa and Xa on Human Bladder Carcinoma Cells;* Blood vol. 7 (May 15), 1989, pp. 1888–1895.

Robert Radcliffe and Yale Nemerson; *Activation and Control of Factor VII by Activated Factor X and Thrombin, Isolation and Characterization of a Single Chain Form of Factor VII;* The Journal of Biological Chemistry, vol. 285, No. 9, Issue of Jan. 25, 1975, pp. 388–395.

Anders H. Pederson, Torben Lund–Hansen, Henrik Bisgaard–Frantzen, Frank Olsen, Lars C. Petersen; *Autoactivation of Human Recombinant Coagulation Factor VII;* Biochemistry 1989, 28, 9331–9336.

Sampath Sridhara, Shu Chaing, Katherine A. High, Morris A Blajchman, Bryan J. Clark; *Activation of a Recombinant Human Factor VII Structural Analogue Alters Its Affinity of Binding to Tissue Factor;* American Journal of Hematology 53:66–71 (1996).

D. Menache and H.R. Roberts; *Summary Report and Recommendations of the Task Force Members and Consultants;* Thrombos. Diathes. haemorrh. (Stuttg.), 1975, 33, 645.

URI Seligsohn, Ariela Zivelin, Shulamith Bar–Shani; *Cold–Promoted Activation of Factor VII: Is it a Problem under Blood Bank Conditions?* Haemostasis 13; 186–191 (1983).

* cited by examiner

*Primary Examiner*—Karen Cochrane Carlson
*Assistant Examiner*—Sheridan Snedden
(74) *Attorney, Agent, or Firm*—Heller Ehrman White & McAuliffe LLP

(57) ABSTRACT

Stable pharmaceutical preparations containing blood coagulation Factor VII is disclosed. The pharmaceutical preparations containing blood coagulation Factor VII are free of coagulation inhibitors and are stable over a wide range of environmental conditions. Also provided are blood coagulation Factor VII preparations having a minimum activity of 50 Units/mg of protein that contain less than 5% activated blood coagulation Factor VII (Factor VIIa). The blood coagulation Factor VII containing preparations may also contain other blood coagulation factors and are free from detectable transmissible human pathogens.

27 Claims, No Drawings

STABLE BLOOD COAGULATION INHIBITOR-FREE FACTOR VII PREPARATION AND METHOD FOR PREPARING SAME

FIELD OF THE INVENTION

The invention relates to a pharmaceutical preparation based on blood coagulation factor VII as well as to a factor VII purification method.

BACKGROUND OF THE INVENTION

The coagulation of blood is triggered by a series of successive reactions of various blood coagulation factors. A deficiency of blood coagulation factors prevents the formation of fibrin from fibrinogen and thus prevents wound closure; the consequence is an increased bleeding risk or hemorrhages, respectively. This is the case if there is a deficiency of vitamin K-dependent blood coagulation factors, such as factors II, VII, IX and X, which is mainly caused by an impaired function of the liver but may also be caused by an inherited deficiency of blood coagulation factors. For a substitution treatment, the corresponding blood coagulation factors are employed. In most instances, a treatment with these preparations leads to a rapid hemostasis.

Factor VII may be recovered from a biological material, such as blood, plasma or cell cultures. If blood or plasma are the starting material, it is mostly obtained together with at least one of the structurally similar factors II, IX or X in purified form. A prothrombin-complex preparation based on factors II, VII, IX and X, or a plasma fraction containing the prothrombin complex, respectively, may likewise be used as the starting material for preparing a further purified factor VII preparation.

For the treatment of patients who suffer from a factor VIII deficiency and who have developed an inhibitor directed against factor VIII, a factor VIIa preparation frequently has been suggested. Highly purified factor VIIa preparations have been described e.g. in EP 0 082 182 and by Hedner et al., (Haemostasis 19, 335–343 (1989)).

Factor VII is relatively easily activatable to factor VIIa. For instance, it has been found that factor VII zymogen is rapidly activated by a number of physiological enzymes, such as factor IXa and factor Xa (Wildgoose et al., Blood, Vol. 73, No. 7, 1989, pp. 1888–1895).

In EP 0 770 625 it has been described that with increasing complexity of the purification procedure, activation of factor VII occurs. Accordingly, the addition of blood coagulation inhibitors, such as antithrombin III/heparin or reversible inhibitors, such as benzamidine, during an affinity-chromatographic purification have been suggested to guard against the risk of a factor VIIa formation.

Likewise, the use of benzamidine protects the factor VII molecule from proteolysis during its isolation throughout the purification procedure, as described by Radcliffe et al., Journal Biological Chemistry 250, 1975, pp. 388–395.

The problem of a factor VII activation, primarily in the presence of positively charged surfaces, e.g. in case of contact with an anion exchanger material, has been described by Pedersen et al. (Biochemistry, 28, 1989, 9331–9336). It has been found that recombinant factor VII could be purified to a homogenous protein in the presence of benzamidine. In the absence of the inhibitor, recombinant factor VII was activated spontaneously. This autocatalytic activation therefore also is a problem in preparations in which not even traces of the physiological activation components are present any longer.

Inhibitors of blood coagulation as such are not desired in a pharmaceutical preparation for treating conditions caused by the deficiency of a blood coagulation factor. Physiological inhibitors, such as antithrombin III or heparin, are being added for stability purposes, i.e. to avoid the activation of the blood coagulation factors in prothrombin complex preparations. Yet, it would be desirable to provide preparations which are sufficiently stable as far as possible without the addition of such inhibitors.

The object of the invention is to provide a pharmaceutical factor VII preparation comprising a portion of activated factor VII as low as possible and a sufficient stability in the absence of inhibitors of blood coagulation. Moreover, a purification method for producing factor VII preparations is to be provided which can be performed efficiently and which is gentle on the proteins, so as to avoid the use of inhibitors, such as benzamidine.

SUMMARY OF THE INVENTION

According to the invention, this object is achieved by a preparation based on blood coagulation factor VII comprising a portion of factor VIIa of less than 5%, having a specific activity of at least 50 U/mg and having a stability in the absence of inhibitors of blood coagulation.

Stability or "stable" is, as known to those of ordinary skill in the blood coagulation arts, defined herein as a preparation containing blood coagulation Factor VII made in accordance with the teachings of the present invention that retains its biological activity after purification and upon standing. Biological activity is measured by activating the Factor VII and measuring its serine protease activity as described in Example 4. A stable Factor VII preparation will retain a serine protease activity of at least 50 units/mg of protein. Units are defined consistent with the Immuno AG Immunochrom FVII:C package insert which is incorporated herein by reference in its entirety.

According to the invention, it is possible for the first time to provide a highly purified factor VII preparation without using the known inhibitors of blood coagulation, in particular without the addition of antithrombin III and/or heparin, benzamidine, soybean trypsin inhibitor, phenyl-methyl-sulfonyl fluoride or EDTA. It has been shown that under the conditions described below, factor VII is not activated during a chromatographic purification procedure, even without the protection against proteolytic enzymes or activation by contact. Thus, the highly purified factor VII preparation does not necessarily contain any one of the inhibitors listed, or less than the detection limit thereof, respectively. As soon as Factor VII a specific activity of at least 50 U/mg has been obtained in the Factor VII preparation, surprisingly it could be shown that factor VII is extremely stable (even with regard to autocatalytic activation processes) whithout requiring the addition of a specific FVII activation inhibitor.

Blood coagulation Factor VII exists as a zymogan (an inactive form of enzyme) in the circulating blood. Factor VII is activated into Factor VIIa by Factor VII specific proteases such as Factors IXa and Xa. Once activated, Factor VIIa exerts a serine protease specific activity that mediates the activation of Factor X.

The stability of the highly purified factor VII is mainly— though not exclusively (cf. Pedersen et al. 1989, regarding an autocatalytic activation)—due to the depletion of factor VII-specific proteases, among them factors IXa and Xa.

Thus, it is ensured that a preparation, such as a pharmaceutical infusion preparation, based on highly purified factor VII comprising at least 50 U/mg of protein, preferably at least 100 U/mg, most preferred at least 500 U/mg of protein, in special cases even at least 1000 U/mg up to the theoretical purity of approximately 2000 U/mg, can remain in a state ready for use over an extended period of time even in the absence of inhibitors of blood coagulation, without the portion of factor VIIa in the preparation increasing beyond the allowable extent.

The preparation according to the invention has a portion of less than 5% of factor VIIa, based on the total amount of factor VII, preferably less than 3%, most preferred less than the detection limit (e.g. in the test according to Seligson et al., Haemostasis 13, 186–191, 1983).

The preparation according to the invention is, e.g., a pharmaceutical grade concentrate which can be used to produce pharmaceutical combination preparations. Such combination preparations may comprise further active substances, such as vitamin K-dependent proteins, among them one or more of blood factors II, IX, X, protein C or protein S. Thus, e.g., a prothrombin complex preparation comprising factors II, VII, IX and X may be made into a partial prothrombin complex by admixing the factor VII preparation of the invention.

Due to its negligible load of contaminants, the factor VII infusion preparation according to the invention may be provided in relatively highly concentrated form, e.g. with a concentration of from 50 to 5000 U/ml. This substantially simplifies the administration of the preparation as a bolus injection or as a short-term infusion.

The stability of the preparation may be tested in the ready for use state so as to determine whether or not it meets the stability criteria according to the invention, i.e. by incubation at room temperature for a period of at least 12 h, preferably more than 30 h. In doing so it can be determined that the preparation according to the invention still comprises less than 5% of factor VIIa.

The preparation according to the invention may also be provided in a durable commercial form, preferably as lyophilized. Upon reconstitution, the extreme stability is shown again, and even during lyophilisation/reconstitution no negative effects occur as regards the (premature) FVII activation. Further forms are deep-frozen preparations or liquid preparations which are stable for an extended storage period, optionally after the addition of stabilizers, such as carrier proteins and/or carbohydrates, preferably at 4° C.

In any case, despite its stability properties (also as regards an autoactivation), factor VII in the preparation according to the invention is an activatable factor VII which can be activated, e.g. in vivo, without any problems and subsequently will be blood-coagulation-active according to native factor VII. Preferably, a native factor VII protein is employed, e.g. human plasmatic factor VII, or human recombinant factor VII. In the recombination of nucleic acids, also factor VII analogs may be used which, in any case, are activatable to an equal or even a higher extent (Sridhara et al., Am. J. Hematology 53, 66–71, 1996).

According to a further aspect, the present invention relates to a method of purifying factor VII from a biological material and producing the factor VII preparation according to the invention by adsorption of factor VII on a chromatographic material, fractionated elution of factor VII with a specific activity of at least 50 U/mg, whereby the elution is carried out with a buffer without the addition of inhibitors of blood coagulation, and recovery of factor VII from the eluate.

DETAILED DESCRIPTION OF THE INVENTION

As starting material for producing the factor VII preparation according to the invention, usually a complex, biological material is used. This includes blood, plasma, plasma fractions, cell cultures, or cell culture fractions, respectively. Yet also a pharmaceutical grade preparation may be used as the starting material which, in addition to factor VII, also comprises further proteins, e.g. a prothrombin complex preparation comprising factors II, VII, IX and X.

To avoid the risk of a transmission of human pathogenic infectious agents, among them viruses transmittable by blood, such as HIV and hepatitis viruses, e.g. HAV, HBV, HCV, HGV, and parvoviruses, yet also the infectious agents of BSE and CJD, a series of measures are taken. Factor VII may be subjected to a method for inactivating, or depleting, respectively, human pathogens each prior to or following chromatographic purification. Preferably, at least two measures are provided which effect the inactivation, or depletion, respectively, due to a different mechanism. Among them are chemical, physico-chemical and physical methods. The methods using virucidal substances preferably are employed prior to or during the chromatographic purification procedure so that the virucidal agent can be removed simultaneously with the purification of factor VII.

Effective measures for inactivating viruses include, e.g., treatment with organic solvents and/or detergents (EP 0 131 740, EP 0 050 061, PCT/AT98/00090), treatment with chaotropic agents (WO 90/15613), heat treatment methods, preferably in lyophilized, dry or humid state (cf. EP 0 159 311), combination methods (EP 0 519 901) and physical methods. The latter cause the inactivation of viruses e.g. by irradiation with light, such as in the presence of photosensitizers (EP 0 471 794 and WO 97/37686).

Human pathogen depletion methods particularly include filtrations using ultrafilters, depth filters or nanofilters (cf. WO 97/40861, AT A 1029/97). Yet, also precipitation steps or other protein purification measures, such as adsorption, contribute to the depletion of possibly present pathogens.

The method according to the invention for purifying factor VII and producing a factor VII preparation comprises at least one chromatographic step. In doing so, factor VII is adsorbed and selectively eluted and fractions are recovered. For the further recovery of factor VII from the eluate, those fractions are chosen in which the specific activity is at least 50 U/mg of protein, preferably at least 100 U/mg.

As elution buffer, preferably a buffer which has a pH in the neutral range, such as in the range of 5–9, preferably 6–7.5, and which has an ionic strength corresponding to a content of NaCl of less than 1 M is employed. As has previously been described, none of the inhibitors of blood coagulation listed are added to the elution buffer. Possibly present physiological inhibitors which exist in the starting material are separated already during adsorption and, optionally, in the subsequent purification of the adsorbed factor VII with a washing buffer so that in any case factor VII is recovered without an inhibitor content. Here, too, the extraordinary stability of the highly purified factor VII is shown which then may be subjected to the further preparation procedures common for producing a pharmaceutical or diagnostic preparation.

Chromatography is performed either in the batch Fee method or in a column. For an improved control of the flow rate or contact period of factor VII with the chromatographic material, the column method is preferred. Preferred materials are carriers with positively charged ligands which may be employed as anion exchangers.

As the anionic exchangers, in principle all the anion exchangers based on carbohydrates or synthetic polymers may be employed which have an affinity to factor VII (prothrombin), such as, e.g., DEAE-Sephacel®, DEAE-Sephadex®, DEAE-Sepharose CL6B®, DEAE-Sepharose Fast Flow@, QAE-Sephadex®, Q-Sepharose Fast Flow®, Q-Sepharose High Performance®, Q-Sepharose Big Beads® (all from Pharmacia);
DEAE-Tris-Acryl®, DEAE-Spherodex®, Q-Hyper-D® (all from Sepracor);
Macroprep DEAE®, Macroprep Q® (all from BioRad); DEAE-Toyopearl®, QAE-Toyopearl®, Toyopearl Super-Q® (all from Tosohaas);
Protein PAK DEAE® (Waters);
Fractogel EMD-TMAE®, Fractogel EMD-DEAE®, Fractogel EMD-DMAE®, Licrospher 1000 TMAE®, Licrospher 1000 DE-AE® and Licrospher 4000 DMAE® (all from MERCK).

In particular, pressure-stable ion exchangers are used, such as, e.g., Fractogel TMAE-EMD, Express IonQ, Sonree 30Q. Surprisingly it has been shown that even on these materials the phenomenon of activation of factor VII does not occur as soon as the period of contact with the anion exchanger material, or the retention time on the column, respectively, is kept short, e.g. less than 5 min. Accordingly, in a column preferably a flow rate of at least 2.5 cm/min, preferably 3.0 cm/min, is chosen for the elution of the adsorbed factor VII.

In most instances, the flow rate corresponds to at least 0.15 column volumes per minute, preferably 0.17, most preferred 0.2 column volumes per minute.

Further materials for chromatographic purification are carriers with ligands which have a specific affinity to factor VII, such as tissue factor, antibodies and peptides. Further preferred materials comprise hydrophobic groups.

As the gel for the hydrophobic interaction chromatography, preferably Phenyl-Sepharose High Performance® (from Pharmacia), yet also other chromatographic gels, such as, e.g., Butyl-Sepharose®, Octyl-Sepharose®, Phenyl-Sepharose®, Phenyl-Sepharose Fast Flow High Sub®, Phenyl Sepharose Fast Flow Low Sub® (all from Pharmacia);
Fractogel TSK-Butyl® (from MERCK);
Macroprep-Methyl-HIC-Support®, Macroprep t-Butyl-HIC-Support® (all from BioRad);
TSK-Gel Butyl Toyopearl®, TSK-Gel Phenyl Toyopearl® and TSK-Gel Ether Toyopearl® (all from Tosohaas) are employed.

As the further carrier materials, also common gel filtration media, such as, e.g., Superose 12, Superdex 75, may be used.

According to a particularly preferred embodiment, also combinations of the chromatographic methods listed are used for producing a factor VII preparation, e.g. the combination of the anion exchange chromatography and hydrophobic interaction chromatography. Optionally, this may be followed by a gel filtration for further purification. Accordingly, an anion exchanger preferably is used as the chromatographic material in the method according to the invention, and a material suitable for hydrophobic chromatography.

The factor VII purified according to the invention may not only be formulated to a pharmaceutical factor VII preparation by the common measures of dialysis/diafiltration, sterile filtration and concentration. Likewise, combination preparations may be provided which contain the factor VII purified according to the invention in addition to other active substances.

In particular, a prothrombin complex preparation may be provided according to the invention which contains at least one of the blood coagulation factors II, IX and X in addition to the highly purified and stable factor VII. These further blood coagulation factors preferably also are purified as individual factors before the combination preparation is provided by appropriate formulation. Such a preparation may be provided with or without inhibitors of blood coagulation. In particular, a heparin content may be provided, according to a recommendation by Menache et al., Thrombosis Diathes. Haemorrh. 33, 645–647 (1975) for producing factor IX-containing pharmaceutical preparations.

The present invention thus also relates to a pharmaceutical preparation comprising a factor VII according to the invention, or a factor VII preparation according to the invention, respectively. This preparation preferably may contain at least one, in particular all, of the blood coagulation factors II, IX and X.

According to a preferred embodiment, the preparation according to the invention is formulated as a pharmaceutical infusion preparation.

Further additions to the preparation according to the invention are preferably antithrombin III and/or Atheplex which is an antithrombin III/heparin complex, prepared, e.g., according to EP 0 129 534.

The invention will be described in more detail by the following examples.

EXAMPLE 1

Purification of Factor VII from Cryosupernatant by Anion Exchange Chromatography on Fractogel TMAE-EMD 340 l of cryosupernatant are adsorbed on $Al(OH)_3$ and eluted with 22.5 g of $Na_2HPO_4 \times 2\ H_2O/l$ (pH 8.5) comprising 1% (v/v) Tween 80 (from plants) and admixed with AT III/heparin complex (350 IU of heparin/kg of eluate, 40 IU of AT III/kg of eluate). The Tween-containing eluate is concentrated approximately 15-fold by ultrafiltration on a membrane having an exclusion limit of ≦30 kD and diafiltered against 10 volumes of 20 mM Tris/HCl (pH 7.0) (Tris buffer). After 0.2 μ filtration and adjustment of the Tween concentration to 15% (v/v), it is incubated for virus inactivation for 3 h at 40° C. The solution diluted with Tris buffer to twice of its volume (3 l) is applied to a BPG100/165 Fractogel TMAE-EMD 650 M-column (from MERCK), subsequently washed with Tris buffer and thereafter washed with Tris buffer at increasing NaCl step gradients (50, 100, 150, 200, 250, 1000 mM/l), eluted and regenerated. The flow rate was at least 2.5 to 3 cm/min at a bed height of 16.5 cm.

Upon the addition of 43.8 IU of heparin/kg and 5.0 IU of ATIII/kg, the 200 mM NaCl eluate (approximately 5 l) was concentrated 60-fold to a protein concentration of 5 mg/ml by ultrafiltration on a membrane having an exclusion limit ≦30 kD. After diafiltration against a solution of 4.8 mM $Na_3$-citrate×2 $H_2O$ and 61.6 mM NaCl/l, the pH is adjusted to a value of 8.0±0.5. The solution is frozen and lyophilized. The lyophilisate is moisturized up to a residual moisture of 7–8% and heated for virus inactivation for 10 h at 60° C. and for 1 h at 80° C.

TABLE 1

| Fraction | Specif. Act.* [U FVII/mg prot.] | FVII-Activation** [U FVIIa/U FVII] | Purification Factor |
|---|---|---|---|
| Plasma | 0.02 | — | 1 |
| Al(OH)$_3$ Tween eluate | 5 | 0.05 | 200 |
| TMAE-eluate | 100 | 0.25 | 5,000 |
| heat-treated lyophilisate | 100 | 0.35 | 5,000 |

*maximum theoretical specific activity: 2000 U of FVII/mg of protein
**complete activation at a FVIIa/FVII ratio of 15–20

EXAMPLE 2
Purification of Factor VII from Cryosupernatant by Anion Exchange Chromatography on Fractogel TMA-EMD and Subsequent Hydrophobic Chromatography on Phenyl-Sepharose It is proceded as in Example 1 as far as to the production of the heat-treated preparation (bulk powder). The bulk powder is dissolved at its original volume with Milli Q-water (from Millipore) (protein concentration approximately 5 mg/ml), its salt content is increased from 60 to 2000 mM NaCl/l and it is applied to an XK50/96 Phenyl-Sepharose-HP column (from Pharmacia) which had been equilibrated in 20 mM Tris/HCl (pH 7.4; 2000 mM NaCl/l). Upon application of 75 ml of FVII bulk powder solution at a flow rate of 10 ml/min, it is subsequently washed with approximately 10 SV of equalibrating buffer, and thereafter it is washed, eluted, and regenerated, respectively, with the following NaCl steps:

1200 mM NaCl/l
850 mM NaCl/l
500 mM NaCl/l
0 mM NaCl/l, each in 20 mM Tris/HCl (pH 7.4)

Approximately 2.8 l of the 850 mM NaCl eluate are subsequently concentrated 5-fold by ultrafiltration on a membrane having an exclusion limit $\leq$ 30 kD and diafiltered against 20 mM ammonium hydrogencarbonate and lyophilized with sublimation of the salts. The salt-free lyophilisate was taken up in 1/50 of the original volume in 0.4% Na$_3$-citrate×2 H$_2$O, 0.8% NaCl (pH 7.0), and re-buffered with slight purification at a flow rate of 2.5 ml/min on a XK26/100 Superose 12 column (from Pharmacia) equilibrated in the same buffer.

TABLE 2

| Fraction | Specif. Act. [U FVII/mg prot.] | FVII-Activation [U FVIIa/U FVII] | FVIII-Yield [%] | Purification Factor |
|---|---|---|---|---|
| Plasma | 0.02 | — | — | 1 |
| Al(OH)$_3$ Tween eluate | 5 | 0.05 | 100 | 200 |
| TMAE-eluate | 100 | 0.25 | 80 | 5,000 |
| heat-treated lyophilisate | 100 | 0.35 | 61 | 5,000 |
| Phenyl-Seph. eluate | 500 | 0.4 | 43 | 25,000 |
| Superose 12-eluate | 1,000 | 0.5 | 35 | 50,000 |

EXAMPLE 3
Influence of the Flow Rate on the Activation of Factor VII on Fractogel TMAE-EMD The purification of FVII from an Al(OH)$_3$ eluate, after virus inactivation with 15% Tween (application 36 mg of protein/ml of gel), was tested on an XK26/16.5 Fractogel TMAE-EMD 650 M column (from Merck) at different flow rates at 22° C. The conditions of chromatography correspond to those in Example 1.

TABLE 3

| Flow rate [cm/min] | Activation [U F7a/UF7] |
|---|---|
| 0.94 | 7.6 |
| 1.88 | 2.65 |
| 2.35 | 0.45 |
| 2.83 | 0.24 |

It has been shown that with an increasing flow rate, the content of activated factor VII decreases. Then, starting from a value of higher than approximately 2.5 to 3 cm/s, the activation rate will remain approximately constant.

EXAMPLE 4
Test for Determining the Stability of the FVII Preparation 4.1. Incubation conditions 100–300 μl aliquots of the FVII-containing eluates of the TMAE, and Phenyl-Sepharose-chromatography, respectively, prepared according to Examples 1 and 2, were incubated for 38 h at 22° C. After this period the serine protaese FVII activity (Immunochrom FVII:C, from IMMUNO AG), the FVIIa coagulation (Staclot VIIa-Rtf, from Diagnostica Stago), and the protein concentration (Bradford) were tested as compared to an aliquot immediately frozen at −20° C.

4.2 Activity tests 4.2.1. IMMUNOCHROM FVII:C

The factor VII activity was kinetically measured under the conditions of a complete activation of FVII by thromboplastin and Ca$^{2+}$ and the subsequent activation of likewise added FX with a chromogenic FXa substrate. It was proceded according to the manufacturer's recommendations.

4.2.2. STACLOT VIIa-rTF

With recombinant, soluble tissue factor, in the presence of phospholipid and FVII deficient plasma alone, the coagulation triggered by FVIIa can be measured with the assistance of a coagulometer. It was proceeded according to the manufacturer's, Diagnostica Stago's, instruction.

4.3 Results

| Fraction | Protein [mg/ml] | U FVII chrom/mg Spec. Act. | U FVIIa Activat. t = 0 | U FVIIa Activat. t = 38 |
|---|---|---|---|---|
| TMAE, 200 mM | 0.04–0.08 | 150–200 | 0.1–0.3 | 0.3–0.8 |
| Phenyl-Seph., 750 mM | 0.02–0.04 | 500–1000 | 0.1–0.2 | 0.1–0.3 |

It has been shown that with the preparations produced according to the invention, there is no activation of FVII worthy of mention, even after a storage for 38 hours at 22° C. This was the more surprising as in the factor VII preparations known so far, always a substantial activation (i.a. also by autocatalysis) occurred which could only be avoided by the addition of specific inhibitors.

The present invention has been described in detail herein and with reference to cited publications. The publications cited are intended to provide the reader with additional information, not deemed essential to patentability. However, all cited publications are herein incorporated by reference in their entirety.

What is claimed is:

1. A stable pharmaceutical preparation comprising:
   blood coagulation factor VII having a protease activity, when activated, of at least 50 U/mg of total protein, wherein blood coagulation factor preparation is free from blood coagulation inhibitors selected from the group consisting of benzamidine, soybean trypsin inhibitor and phenyl-methyl-sulfonyl fluoride, and contains no more than approximately 5% of activated blood coagulation factor VII.

2. The stable pharmaceutical preparation of claim 1, wherein the blood coagulation factor VII has a protease activity, when activated, of greater than 100 Units/mg of total protein.

3. The stable pharmaceutical preparation of claim 1, wherein the blood coagulation factor VII is present in an amount of between approximately 5 U/mL to approximately 5,000 U/mL.

4. The stable pharmaceutical preparation of claim 1, wherein the preparation is lyophilized.

5. The stable pharmaceutical preparation of claim 4, wherein the preparation is stable for at least 12 hours after reconstitution.

6. The stable pharmaceutical preparation of claim 1, wherein the blood coagulation factor VII is a recombinant protein.

7. The stable pharmaceutical preparation of claim 1, wherein the blood coagulation factor VII is recovered from normal human plasma.

8. The stable pharmaceutical preparation of claim 7, wherein the blood coagulation factor preparation has no detectable transmissible human pathogens.

9. A method for preparing a stable pharmaceutical preparation comprising:
   absorbing blood coagulation factor VII from a biological material onto a chromatographic substrate;
   selectively eluting the absorbed blood coagulation factor VII from the chromatographic substrate using an elution buffer that is free from blood coagulation inhibitors selected from the group consisting of benzamidine, soybean trypsin inhibitor and phenyl-methyl-sulfonyl fluoride; and
   selecting an eluate having a protease activity of at least 50 U/mg of total protein, when activated, and
   preparing the pharmaceutical preparation from the eluate, wherein the pharmaceutical preparation contains no more than approximately 5% activated blood coagulation factor VII and is free from blood coagulation inhibitors selected from the group consisting of benzamidine, soybean trypsin inhibitor and phenyl-methyl-sulfonyl fluoride.

10. The method for preparing a stable pharmaceutical preparation of claim 9, wherein the elution buffer has a pH of between approximately 5.0 to approximately 9.0.

11. The method for preparing a stable pharmaceutical preparation of claim 10, wherein the elution buffer has a pH of between approximately 6.0 to approximately 7.5.

12. The method for preparing a stable pharmaceutical preparation of claim 9, wherein the chromatographic substrate is an anion exchange material and the selective elution being performed using a chromatography column and a chromatography column flow rate of at least 0.15 column volumes per minute.

13. The method for preparing a stable pharmaceutical preparation of claim 12, wherein the flow rate is between approximately 0.17 to 2.0 column volumes per minute.

14. The method for preparing a stable pharmaceutical preparation of claim 9, wherein the chromatographic substrate is an immunoaffinity column specific for factor VII.

15. The method for preparing a stable pharmaceutical preparation of claim 9, wherein the chromatographic substrate is a material having hydrophobic groups.

16. The method for preparing a stable pharmaceutical preparation of claim 9, wherein the chromatographic substrate is a hydrogel.

17. The method for preparing a stable pharmaceutical preparation of claim 9, wherein the biological material is selected from the group consisting of blood, plasma, a plasma fraction, a cell culture and a cell culture fraction.

18. The method for preparing a stable pharmaceutical preparation of claim 12, further comprising absorbing the eluate having a protease activity of at least 50 U/mg of total protein onto a second chromatographic substrate having hydrophobic groups and selectively eluting the absorbed eluate from the chromatographic substrate having hydrophobic groups.

19. A stable pharmaceutical preparation made according to claim 9.

20. A stable pharmaceutical preparation made according to claim 18.

21. A stable pharmaceutical preparation comprising:
   blood coagulation factor VII having a protease activity, when activated, of at least 50 U/mg of total protein, wherein the blood coagulation factor preparation is free from blood coagulation inhibitors selected from the group consisting of benzamidine, soybean trypsin inhibitor and phenyl-methyl-sulfonyl fluoride, and contains no more than approximately 5% of activated blood coagulation factor VII; and
   at least one additional coagulation factor.

22. The stable pharmaceutical preparation of claim 21, wherein the additional blood coagulation factor is selected from the group consisting of factor II, factor IX and factor X.

23. A method for preparing a stable pharmaceutical preparation comprising:
   absorbing blood coagulation factor VII from a biological material onto an anionic chromatographic column;
   selectively eluting the absorbed blood coagulation factor VII from the chromatographic column at a flow rate of between approximately 0.17 to 2.0 column volumes per minute using an elution buffer having a pH of between approximately 6.0 to 7.5, wherein the elution buffer is free from blood coagulation inhibitors selected from the group consisting of benzamidine, soybean trypsin inhibitor and phenyl-methyl-sulfonyl fluoride; and
   selecting an eluate having a protease activity of at least 50 U/mg of total protein, when activated, and
   preparing the pharmaceutical preparation from the eluate, wherein the pharmaceutical preparation contains no more than approximately 5% activated blood coagulation factor VII and is free from blood coagulation inhibitors selected from the group consisting of benzamidine, soybean trypsin inhibitor and phenyl-methyl-sulfonyl fluoride.

24. The method for preparing a stable pharmaceutical preparation of claim 23, wherein the biological material is selected from the group consisting of blood, plasma, a plasma fraction, a cell culture and a cell culture fraction.

25. The method for preparing a stable pharmaceutical preparation of claim 23, further comprising absorbing the eluate having a protease activity of at least 50 U/mg of total protein onto a second chromatographic substrate having hydrophobic groups and selectively eluting the absorbed eluate from the chromatographic substrate having hydrophobic groups.

26. A stable pharmaceutical preparation made according to claim 23.

27. A stable pharmaceutical preparation made according to claim 25.

* * * * *